US009381242B2

(12) United States Patent
Nozaki et al.

(10) Patent No.: US 9,381,242 B2
(45) Date of Patent: Jul. 5, 2016

(54) ADJUVANT COMPOSITION CONTAINING CITRULLINE

(75) Inventors: Chikateru Nozaki, Kumamoto (JP);
Kazuyoshi Kaminaka, Kumamoto (JP);
Junichi Matsuda, Kumamoto (JP)

(73) Assignee: THE CHEMO—SERO—THERAPEUTIC RESEARCH INSTITUTE, Kumamoto-shi (JP)

( * ) Notice: Subject to any disclaimer, the term of this patent is extended or adjusted under 35 U.S.C. 154(b) by 0 days.

(21) Appl. No.: 14/004,308

(22) PCT Filed: Mar. 9, 2012

(86) PCT No.: PCT/JP2012/056132
§ 371 (c)(1),
(2), (4) Date: Sep. 10, 2013

(87) PCT Pub. No.: WO2012/124631
PCT Pub. Date: Sep. 20, 2012

(65) Prior Publication Data
US 2014/0065179 A1 Mar. 6, 2014

(30) Foreign Application Priority Data
Mar. 11, 2011 (JP) ................................. 2011-053658

(51) Int. Cl.
*A61K 45/00* (2006.01)
*A61K 39/145* (2006.01)
(Continued)

(52) U.S. Cl.
CPC ............. *A61K 39/39* (2013.01); *A61K 39/0007* (2013.01); *A61K 39/12* (2013.01); *A61K 39/145* (2013.01); *A61K 2039/55511* (2013.01); *A61K 2039/55516* (2013.01); *C12N 2760/16134* (2013.01)

(58) Field of Classification Search
None
See application file for complete search history.

(56) References Cited

U.S. PATENT DOCUMENTS

2001/0056068 A1 12/2001 Chwalisz et al.
2002/0143060 A1 10/2002 Kohchi et al.
(Continued)

FOREIGN PATENT DOCUMENTS

| JP | 53-075387 A | 7/1978 |
|----|-------------|--------|
| JP | 63-068091 A | 3/1988 |

(Continued)

OTHER PUBLICATIONS

Orea-Tejeda et al., "The effect of L-arginine and citrulline on endothelial function in patients in heart failure with preserved ejection fraction," Cardiology Journal, vol. 17, No. 5: 464-470 (2010).*

(Continued)

*Primary Examiner* — Benjamin P Blumel
*Assistant Examiner* — M. Franco Salvoza
(74) *Attorney, Agent, or Firm* — Oblon, McClelland, Maier & Neustadt, L.L.P.

(57) ABSTRACT

A novel adjuvant composition is provided that is excellent in safety and convenience as compared to the conventional adjuvant such as Alum. An adjuvant composition comprising citrullines, which are water soluble substance present in the living body, and/or a salt thereof; a vaccine composition comprising said adjuvant composition and an antigen; a process for preparing said adjuvant composition and said vaccine composition; and a method for administering said adjuvant composition and said vaccine composition are provided.

20 Claims, 1 Drawing Sheet

(51) Int. Cl.
*A61K 39/39* (2006.01)
*A61K 39/12* (2006.01)
*A61K 39/00* (2006.01)

(56) References Cited

U.S. PATENT DOCUMENTS

| | | | |
|---|---|---|---|
| 2003/0207324 A1* | 11/2003 | Humphreys et al. | 435/7.1 |
| 2004/0062773 A1* | 4/2004 | Santiago et al. | 424/185.1 |
| 2010/0291122 A1 | 11/2010 | Matsuda et al. | |
| 2012/0231025 A1* | 9/2012 | Sahner et al. | 424/185.1 |
| 2012/0244184 A1 | 9/2012 | Kaminaka et al. | |
| 2013/0011424 A1* | 1/2013 | Maksyutov et al. | 424/185.1 |

FOREIGN PATENT DOCUMENTS

| | | |
|---|---|---|
| JP | 2002-226370 A | 8/2002 |
| WO | WO 2007/015167 A2 | 2/2007 |
| WO | WO 2008075371 A2 * | 6/2008 |
| WO | WO 2008/133208 A1 | 11/2008 |
| WO | WO 2009053535 A2 * | 4/2009 |
| WO | WO 2010/033424 A2 | 3/2010 |
| WO | WO 2010/078556 A1 | 7/2010 |
| WO | WO 2011/024748 A1 | 3/2011 |

OTHER PUBLICATIONS

Banerjee et al., "Combined inhalational and oral supplementation of ascorbic acid may prevent influenza pandemic emergency," Nutrition 26: 128-132 (2010).*

Flora et al., "Beneficial effect of combined administration of some naturally occurring antioxidants (vitamins) and thiol chelators in the treatment of chronic lead intoxication," Chemico-Biological Interactions, vol. 145, Issue 3: 267-280 (2003).*

Baigent et al., "Genetic Analysis Reveals That Both Haemaglutinin and Neuraminidase Determine the Sensitivity of Naturally Occurring Avian Influenza Viruses to Zanamavir in Vitro," Virology 263: 323-338 (1999).*

Cormio et al., "Oral L-Citrulline Supplementation Improves Erection Hardness in Men With Mild Erectile Dysfunction," Urology 77: 119-122 (2011).*

Lassala et al., "Intravenous Administration of L-Citrulline to Pregnant Ewes is More Effective Than L-Arginine for Increasing Arginine Availability in the Fetus," J. Nutr. 139: 660-665 (2009).*

Extended European Search Report issued Aug. 7, 2014 in Patent Application No. 12757500.9.

Jeff Boyle, et al., "The utility of ISCOMATRIX™ adjuvant for dose reduction of antigen for vaccines requiring antibody responses", Vaccine, vol. 25, No. 14, XP0052925101, Mar. 15, 2007, pp. 2541-2544.

Erik B. Lindblad, "Aluminum adjuvants—in retrospect and prospect", Vaccine, vol. 22, No. 27-28, XP004526946, Sep. 9, 2004, pp. 3658-3668.

Karin Lovgren Bengtsson, et al, "Adjuvant activity of iscoms; effect of ratio and co-incorporation of antigen and adjuvant", Vaccine, vol. 14, No. 8, XP004069558, Jun. 1, 1996, pp. 753-760.

Office Action and Search Report issued on Aug. 4, 2014 in the corresponding Chinese Patent Application No. 201280022634.6 (with English Translation).

International Search Report issued Apr. 24, 2012 in PCT/JP2012/056132.

English translation of the International Preliminary Report on Patentability issued Sep. 26, 2013 in PCT/JP2012/056132.

English translation of the Written Opinion issued Apr. 24, 2012 in PCT/JP2012/056132.

Miho Kizaki, "L-Citrulline no Seiri Kino," New Food Industry, vol. 51, No. 9, 2009, 6 Pages, with English Abstract.

Vishal Bansal, et al. "Citrulline Can Preserve Proliferation and Prevent the Loss of CD3 Zeta Chain Under Conditions of Low Arginine," Journal of Parenteral and Enteral Nutrition, vol. 28, No. 6, Nov. 2004, pp. 423-430.

Frank Mattner, et al. "Vaccination with Poly-L-Arginine as Immunostimulant for Peptide Vaccines: Induction of Potent and Long-Lasting T-Cell Responses against Cancer Antigens," Cancer Research, vol. 62, No. 5, Mar. 1, 2002, pp. 1477-1480.

M.O. Meneguello, et al. "Effect of arginine, ornithine and citrulline supplementation upon performance and metabolism of trained rats," Cell Biochemistry and Fuction, vol. 21, 2003, pp. 85-91.

Santhanam A.V. Raghavan, et al., "L-Citrulline mediated relaxation in the control and lipopolysaccharide-treated rat aortic rings" European Journal of Pharmacology, vol. 431, 2001, pp. 61-69.

Pel Yan Chen, et al., "L-Arginine Abrogates Salt-sensitive Hypertension in Dahl/Rapp Rats" Journal of Clinical Investigation, vol. 88, Nov. 1991, pp. 1559-1567.

Sitish Rattan, et al., "L-Citrulline Recycling in Opossum Internal Anal Sphincter Relaxation by Nonadrenergic, Noncholinergic Nerve Stimulation" Gastroenterology, vol. 112, Apr. 1997, pp. 1250-1259.

Alton C. Kurtz, "A Simple Synthesis of dl-Citrulline" The Journal of Biological Chemistry, vol. 122, 1938, pp. 477-484.

Sidney W. Fox, et al., "The Synthesis of d,1-Citrulline From Non-Biological Precursors," The Journal of Organic Chemistry, vol. 6, 1941, pp. 410-416.

Japanese Office Action dated Aug. 4, 2015 in corresponding European Patent Application No. 12 757 500.9, 4 pp.

* cited by examiner

```
                          SEQUENCE LISTING

<160> NUMBER OF SEQ ID NOS: 6

<210> SEQ ID NO 1
<211> LENGTH: 23
<212> TYPE: PRT
<213> ORGANISM: Influenza A virus

<400> SEQUENCE: 1

Ser Leu Leu Thr Glu Val Glu Thr Pro Ile Arg Asn Glu Trp Gly Cys
1               5                  10                  15

Arg Cys Asn Asp Ser Ser Asp
            20

<210> SEQ ID NO 2
<211> LENGTH: 26
<212> TYPE: PRT
<213> ORGANISM: Artificial Sequence
<220> FEATURE:
<223> OTHER INFORMATION: A modified peptide obtained by inserting
      cysteines into the peptide derived from Influenza virus M2 protein

<400> SEQUENCE: 2

Ser Leu Leu Thr Glu Val Glu Thr Pro Ile Arg Asn Glu Trp Gly Cys
1               5                  10                  15

Arg Cys Asn Cys Asp Cys Ser Cys Ser Asp
            20                  25

<210> SEQ ID NO 3
<211> LENGTH: 42
<212> TYPE: PRT
<213> ORGANISM: Homo sapiens

<400> SEQUENCE: 3

Asp Ala Glu Phe Arg His Asp Ser Gly Tyr Glu Val His His Gln Lys
1               5                  10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 4
<211> LENGTH: 28
<212> TYPE: PRT
<213> ORGANISM: Artificial Sequence
<220> FEATURE:
<223> OTHER INFORMATION: Synthesized Peptide

<400> SEQUENCE: 4

Asp Ala Glu Phe Arg His Asp Ser Gly Tyr Glu Val His His Gln Lys
1               5                  10                  15

Leu Val Phe Phe Ala Glu Asp Val Gly Ser Asn Lys
            20                  25

<210> SEQ ID NO 5
<211> LENGTH: 29
<212> TYPE: PRT
<213> ORGANISM: Artificial Sequence
<220> FEATURE:
```

```
<223> OTHER INFORMATION: Synthesized Peptide

<400> SEQUENCE: 5

Asp Ala Glu Phe Arg His Asp Ser Gly Tyr Glu Val His His Gln Lys
1               5                   10                  15

Leu Val Phe Phe Ala Glu Asp Val Gly Ser Asn Lys Cys
            20                  25

<210> SEQ ID NO 6
<211> LENGTH: 40
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40
```

ADJUVANT COMPOSITION CONTAINING CITRULLINE

CROSS REFERENCE TO RELATED APPLICATIONS

The present application is a 35 U.S.C. §371 national stage patent application of International patent application PCT/JP2012/056132, filed on Mar. 9, 2012, published as WO/2012/124631 on Sep. 20, 2012, the text of which is incorporated by reference, and claims the benefit of the filing date of Japanese application no. 2011-053658, filed on Mar. 11, 2011, the text of which is also incorporated by reference.

TECHNICAL FIELD

The present invention relates to an adjuvant composition comprising citrullines, an adjuvant composition comprising citrullines and an antioxidant (e.g. ascorbic acid), and a vaccine composition comprising the adjuvant composition and an antigen.

BACKGROUND ART

A vaccine may comprise an adjuvant, a diluent, a preservative, a stabilizing agent and a buffer together with an antigenic substance. In particular, an adjuvant is a substance that is administered together with an antigen and may enhance an immunological response to the antigen administered. An adjuvant may act in various ways depending on its kind, e.g. (1) it adsorbs an antigen to accelerate its intake into antigen-presenting cells; (2) it retains an antigen in a local area for a long period of time to release the antigen gradually so as to prolong antigenic stimulation; or (3) it directly activates immunocompetent cells. Thus, an adjuvant is very advantageous in reducing a dose and the number of administration of a vaccine or an amount of an antigen contained in a vaccine. Therefore, there have hitherto been made a variety of studies concerning an adjuvant that may enhance the action of a vaccine. However, adjuvants that have actually been used in medical settings are quite few.

A typical adjuvant includes aluminum hydroxide (hereinafter referred to as "Alum adjuvant") that has been used in various vaccines. Alum adjuvant however is not an ideal adjuvant from the viewpoint of inconvenience that it can hardly be mixed uniformly with an antigen due to its insolubility and that it cannot easily be combined with a device for nasal or transdermal administration. Other than Alum adjuvant, there are adjuvants using squalene or MPL (monophosphoryl lipid). However, although they may exert a strong adjuvant activity, they exhibit severe adverse side effects and are disadvantageously insoluble in water. Thus, in medical settings, there is a desire for development of an adjuvant that may induce an elevated immunological reaction in human body, may exert few adverse side effects, and may exhibit enhanced convenience.

On the other hand, citrulline, a kind of an amino acid, is one of compounds that constitute the urea cycle and is prevalent among animals, in particular, mammals [Chemical formula: $C_6H_{13}N_3O_3$, 2-amino-5-(carbamoylamino)-pentanoic acid, Molecular weight: 175.2 g/mol]. Citrulline was found from watermelon in Japan in 1930 and is named after *Citrullus vulgaris*, a scientific name of watermelon.

Although citrulline is not an amino acid constituting a protein in the living body, it is one of intermediate compounds of the urea cycle. Citrulline is produced from arginine together with nitrogen oxide (NO) known as a substance with a vasodilating activity and is condensed with aspartic acid to regenerate arginine. Citrulline is known to exhibit useful activities such as acceleration of ammonium metabolism (Non-patent reference 1), improvement of blood flow due to vasodilation (Non-patent reference 2), decrease in blood pressure (Non-patent reference 3), neurotransmission (Non-patent reference 4) and elimination of active oxygen (Patent reference 1).

Therefore, citrulline has been approved as food material such as supplement in Japan in 2007. Citrulline has been used overseas earlier. Citrulline is commercially available as supplements for improvement of blood flow, prevention of arteriosclerosis and energy enhancement in the U.S. and citrulline-malate is commercially available as a medicament for recovery from fatigue in Europe.

Notwithstanding that a variety of activities of citrulline have been reported, it is not known that citrulline has an adjuvant activity. A vaccine comprising citrulline and an antigen as well as an adjuvant comprising citrulline have not been reported. Also, there is no report as to finding that citrulline and an antioxidant may be used together as an adjuvant.

Patent reference 1: Japanese Patent Publication No. 2002-226370
Patent reference 2: Japanese Patent Publication No. 53-075387
Patent reference 3: Japanese Patent Publication No. 63-068091
Patent reference 4: WO 2011024748
Patent reference 5: WO 2008133208
Non-patent reference 1: Cell Biochemistry and Function, "Effect of arginine, ornithine and citrulline supplementation upon performance and metabolism of trained rats", 2003, Vol. 21, p. 85-91
Non-patent reference 2: European Journal of Pharmacology, "L-Citrulline mediated relaxation in the control and lipopolysaccharide-treated rat aortic rings", 2001, Vol. 431, p. 61-69
Non-patent reference 3: Journal of Clinical Investigation, "L-arginine abrogates salt-sensitive hypertension in Dahl/Rapp rats", 1991, Vol. 88, p. 1559-1567
Non-patent reference 4: Gastroenterology, "L-citrulline recycling in opossum internal anal sphincter relaxation by nonadrenergic, noncholinergic nerve stimulation", 1997, Vol. 112, p. 1250-1259
Non-patent reference 5: The Journal of Biological Chemistry, "A SIMPLE SYNTHESIS OF dl-CITRULLINE", 1938, Vol. 122, p. 477-p 484
Non-patent reference 6: The Journal of Organic Chemistry, "THE SYNTHESIS OF d,l-CITRULLINE FROM NON-BIOLOGICAL PRECURSORS", 1941, Vol. 6, p. 410-416

DISCLOSURE OF THE INVENTION

Technical Problem to be Solved by the Invention

The present inventors have investigated an adjuvant that would obviate drawbacks of Alum adjuvant (inconvenience due to insolubility etc.) and of new adjuvants such as squalene (severe adverse side effects). Thus, the present invention aims at providing an adjuvant that may enhance immunogenicity of an antigen, is highly safe to human body and has improved convenience.

Means for Solving the Problems

Viewing the above circumstances, the present inventors have earnestly studied an adjuvant that may exert a sufficient antibody-producing activity, is highly safe and has improved convenience and as a result have found an extremely novel finding hitherto not reported that citrulline may exert an excellent adjuvant activity. In addition, citrulline, as water soluble substance, may easily be compounded with an antigen and is highly safe since it is contained in the living body of mammals or in a variety of food products. Therefore, in accordance with the present invention, it becomes possible to provide a vaccine or an adjuvant that are excellent in an antibody-producing activity, safety and convenience by using citrulline.

The present invention included the following inventions.

[1] An adjuvant composition comprising citrullines.

[2] The adjuvant composition according to [1] wherein said citrullines are one or two or more selected from the group consisting of L-citrulline, D-citrulline, L-thiocitrulline, L-thiohomocitrulline, S-methyl-L-thio-citrulline and S-ethyl-L-thiocitrulline.

[3] The adjuvant composition according to [2] wherein said citrullines are L-citrulline or D-citrulline.

[4] The adjuvant composition according to any of [1] to [3] wherein said citrullines are contained at 1 mg/mL to 50 mg/mL.

[5] The adjuvant composition according to any of [1] to [4] which is one for a peptide antigen.

[6] The adjuvant composition according to any of [1] to [5] which further comprises an antioxidant.

[7] The adjuvant composition according to [6] wherein said antioxidant is ascorbic acid.

[8] The adjuvant composition according to [6] or [7] wherein a weight ratio of said citrullines and said antioxidant is 1:2 to 2:1.

[9] The adjuvant composition according to any of [6] to [8] which comprises said antioxidant at 1 to 10 mg/mL.

[10] A vaccine composition which comprises the adjuvant composition comprising citrullines as set forth in any of [1] to [9] and an antigen.

[11] The vaccine composition according to [10] wherein a weight ratio of said antigen and said citrullines is 1:N wherein N is 100 or more.

[12] The vaccine composition according to [10] wherein said antigen is an antigen from influenza virus.

[13] The vaccine composition according to [12] wherein said antigen from influenza virus is at least one or two or more selected from the group consisting of hemagglutinin (HA), neuraminidase (NA), matrix 1 (M1), matrix 2 (M2) and nuclear protein (NP).

[14] The vaccine composition according to [13] wherein said antigen from influenza virus is hemagglutinin (HA).

[15] The vaccine composition according to [13] wherein said antigen from influenza virus is matrix 2 (M2).

[16] The vaccine composition according to any of [12] to [15] wherein a weight ratio of said antigen from influenza virus and said citrullines is 1:N wherein N is 300 or more.

[17] The vaccine composition according to [10] wherein said antigen is a peptide.

[18] The vaccine composition according to [17] wherein a weight ratio of said peptide and said citrullines is 1:N wherein N is 100 or more.

[19] The vaccine composition according to [17] wherein said peptide is an M2e peptide, an M2e peptide with addition or insertion of one or several cysteine(s), or an M2e peptide with addition of a cysteine-containing peptide.

[20] The vaccine composition according to [19] wherein said peptide is a synthetic peptide prepared by inserting a cysteine residue into positions between No. 20 and No. 21, between No. 21 and No. 22, and between No. 22 and No. 23, respectively, counted from the N-terminus of an M2e peptide.

[21] The vaccine composition according to [19] or [20] wherein a weight ratio of said M2e peptide and said citrullines is 1:N wherein N is 200 or more.

[22] The vaccine composition according to [17] wherein said peptide is an amyloid β (Aβ) peptide, a peptide consisting of an amino acid sequence of a portion of an amyloid β (Aβ) peptide, or said peptides with addition or insertion of one or several cysteine(s).

[23] The vaccine composition according to [22] wherein said peptide is a peptide consisting of 28 amino acid residues counted from the N-terminus of an amyloid β (Aβ) peptide, to the C-terminus of which one cysteine residue is added.

[24] The vaccine composition according to [22] or [23] wherein a weight ratio of said amyloid β peptide and said citrullines is 1:N wherein N is 100 or more.

[25] The vaccine composition according to [10] wherein said antigen is a peptide consisting of at least one or two or more of an amino acid sequence selected from the group consisting of SEQ ID NO: 1, SEQ ID NO: 2, SEQ ID NO: 3, SEQ ID NO: 4 and SEQ ID NO: 5.

[26] A process for preparing a vaccine with an enhanced ability to produce an antibody to an antigen contained in said vaccine, which comprises adding citrullines as an adjuvant to a vaccine.

[27] The process according to [26] wherein said citrullines are one or two or more selected from the group consisting of L-citrulline, D-citrulline, L-thiocitrulline, L-thiohomocitrulline, S-methyl-L-thio-citrulline and S-ethyl-L-thiocitrulline.

[28] The process according to [27] wherein said citrullines are L-citrulline or D-citrulline.

[29] The process according to any of [26] to [28] wherein said citrullines are added at 1 mg/mL to 50 mg/mL.

[30] The process according to any of [26] to [29] wherein a weight ratio of said antigen and said citrullines is 1:N wherein N is 100 or more.

[31] The process according to any of [26] to [29] wherein said antigen is an antigen from influenza virus.

[32] The process according to [31] wherein said antigen from influenza virus is at least one or two or more selected from the group consisting of hemagglutinin (HA), neuraminidase (NA), matrix 1 (M1), matrix 2 (M2) and nuclear protein (NP).

[33] The process according to [32] wherein said antigen from influenza virus is hemagglutinin (HA).

[34] The process according to [32] wherein said antigen from influenza virus is matrix 2 (M2).

[35] The process according to any of [31] to [34] wherein a weight ratio of said antigen from influenza virus and said citrullines is 1:N wherein N is 300 or more.

[36] The process according to [26] wherein said antigen is a peptide.

[37] The process according to [36] wherein a weight ratio of said peptide and said citrullines is 1:N wherein N is 100 or more.

[38] The process according to [36] wherein said peptide is an M2e peptide, an M2e peptide with addition or insertion of one or several cysteine(s), or an M2e peptide with addition of a cysteine-containing peptide.

[39] The process according to [38] wherein said peptide is a synthetic peptide prepared by inserting a cysteine residue into positions between No. 20 and No. 21, between No. 21 and No. 22, and between No. 22 and No. 23, respectively, counted from the N-terminus of an M2e peptide.

[40] The process according to [38] or [39] wherein a weight ratio of said M2e peptide and said citrullines is 1:N wherein N is 200 or more.

[41] The process according to [36] wherein said peptide is an amyloid β (Aβ) peptide, a peptide consisting of an amino acid sequence of a portion of an amyloid β (Aβ) peptide, or said peptides with addition or insertion of one or several cysteine(s).

[42] The process according to [41] wherein said peptide is a peptide consisting of 28 amino acid residues counted from the N-terminus of an amyloid β (Aβ) peptide, to the C-terminus of which one cysteine residue is added.

[43] The process according to [41] or [42] wherein a weight ratio of said amyloid β peptide and said citrullines is 1:N wherein N is 100 or more.

[44] The process according to [26] wherein said antigen is a peptide consisting of at least one or two or more of an amino acid sequence selected from the group consisting of SEQ ID NO: 1, SEQ ID NO: 2, SEQ ID NO: 3, SEQ ID NO: 4 and SEQ ID NO: 5.

[45] The process according to any of [26] to [44] which comprises adding also an antioxidant in addition to citrullines.

[46] The process according to [45] wherein said antioxidant is ascorbic acid.

[47] The process according to [45] or [46] wherein said citrullines and said antioxidant are added at a weight ratio of is 1:2 to 2:1.

[48] The process according to any of [45] to [47] wherein said antioxidant is added at 1 to 10 mg/mL.

[49] Use of citrullines as an adjuvant.

[50] The use according to [49] wherein said citrullines are one or two or more selected from the group consisting of L-citrulline, D-citrulline, L-thiocitrulline, L-thiohomocitrulline, S-methyl-L-thio-citrulline and S-ethyl-L-thiocitrulline.

[51] The use according to [50] wherein said citrullines are L-citrulline or D-citrulline.

[52] The use according to any of [49] to [51] wherein said citrullines are added to a vaccine at 1 mg/mL to 50 mg/mL.

[53] The use according to any of [49] to [52] in which an antioxidant is also used.

[54] The use according to [53] wherein said antioxidant is ascorbic acid.

[55] The use according to [53] or [54] wherein said citrullines and said antioxidant are added to a vaccine at a weight ratio of 1:2 to 2:1.

[56] The use according to any of [53] to [55] wherein said antioxidant is added to a vaccine at 1 to 10 mg/mL.

Effects of the Invention

In accordance with the present invention, by administering citrullines and an antigen together, it becomes possible to enhance immunogenicity as compared to administration of an antigen alone. It was found that citrullines exerted an antibody-producing effect to the same extent as that of the conventional adjuvant (Alum adjuvant) and a higher antibody-producing effect than Alum adjuvant when an antigen is a peptide. It was further found that an antibody-producing effect was improved by using a combination of citrullines and an antioxidant (e.g. ascorbic acid) as an adjuvant as compared to the use of citrullines alone as an adjuvant.

Besides, since citrulline is water soluble substance naturally present in the living body, it may easily be compounded with an antigen as compared to the conventional Alum adjuvant or oily adjuvants to thereby reduce the risk of adverse side effects. Therefore, an adjuvant composition comprising citrullines and a vaccine composition of the present invention have improved convenience and are highly safe to the human body. Furthermore, since citrullines may be prepared in mass production by chemical synthesis or microorganisms, they may be provided as an adjuvant for a vaccine in a scale of production of pharmaceutical preparations.

BEST MODE FOR CARRYING OUT THE INVENTION

The first embodiment of the present invention is an adjuvant composition comprising citrullines.

Citrullines contained in an adjuvant composition of the present invention include citrulline, citrulline derivatives and a salt of citrulline. Citrulline includes L-citrulline and D-citrulline, preferably L-citrulline. Citrulline derivatives include L-thiocitrulline, L-thiohomocitrulline, S-methyl-L-thiocitrulline and S-ethyl-L-thiocitrulline. Thus, citrullines of the present invention include L-citrulline, D-citrulline, L-thiocitrulline, L-thiohomocitrulline, S-methyl-L-thiocitrulline and S-ethyl-L-thiocitrulline.

Citrullines contained in an adjuvant composition of the present invention may be a salt of citrulline. A salt of citrulline includes an acid addition salt, a metal salt, an ammonium salt, an organic amine addition salt, an amino acid addition salt, and the like. An acid addition salt includes an inorganic acid salt such as hydrochloride, sulfate, nitrate and phosphate and an organic acid salt such as acetate, maleate, fumarate, citrate, malate, lactate, α-ketoglutarate, gluconate and caprylate. A metal salt includes an alkali metal salt such as sodium salt and potassium salt; an alkaline earth metal salt such as magnesium salt and calcium salt; aluminum salt, zinc salt, and the like. An ammonium salt includes a salt of ammonium, tetramethylammonium, and the like. An organic amine salt includes a salt of morpholine, piperidine, and the like. An amino acid addition salt includes a salt of glycine, phenylalanine, lysine, aspartic acid, glutamic acid, and the like.

Citrullines may be obtained by chemical synthesis, fermentation, and the like. Chemical synthesis of citrullines includes, for instance, those described in Gastroenterology, 1997, Vol. 112, p. 1250-1259 (Non-patent reference 4) and The Journal of Biological Chemistry, 1938, Vol. 122, p. 477-p 484 (Non-patent reference 5). Fermentation production of L-citrulline includes, for instance, those disclosed in Japanese Patent Publication No. 53-075387 (Patent reference 2) and Japanese Patent Publication No. 63-068091 (Patent reference 3). Citrullines may also be obtained by purchasing commercially available products, including by way of example L-citrulline (Sigma-Aldrich: Code No. 27510 and C7629), L-thiocitrulline (Sigma-Aldrich: Code No. 88544, Wako Pure Chemical Industries, Ltd.: Code No. 205-13861) and S-methyl-L-thiocitrulline (Wako Pure Chemical Industries, Ltd.: Code No. 139-12611).

A concentration of citrullines contained in an adjuvant composition of the present invention may vary as appropriate depending upon the kind of an antigen, a dosage form, a way of administration, patients, and the like. An adjuvant composition of the present invention may comprise citrullines at A mg/mL to B mg/mL wherein A and B are different numeric selected from the group consisting of 1, 5, 10, 15, 20, 25, 30, 35, 40, 45, 50, 55, 60, 65, 70, 75, 80, 85, 90, 95 and 100 and wherein A is smaller than B.

A dose of citrullines using an adjuvant composition of the present invention may vary as appropriate depending upon the kind of an antigen, a dosage form, a way of administration, and the like.

An adjuvant composition of the present invention may comprise an antioxidant in addition to citrullines. An antioxidant includes, for instance, ascorbic acid (vitamin C), α-tocopherol (vitamin E), glutathione, N-acetylcysteine, butylhydroxyanisole, catechin, quercetin, uric acid, bilirubin, glucose, flavonoid, ceruloplasmine, albumin, ferritin, metallothionein, superoxide dismutase, glutathione peroxidase, glutathione transferase, catalase and thioredoxin, preferably, ascorbic acid and α-tocopherol.

In case that a vaccine composition or an adjuvant composition comprises an antioxidant in addition to citrullines, a weight ratio of citrullines and an antioxidant may be 1:2 to 2:1, preferably 1:1. An adjuvant composition of the present invention may comprise an antioxidant at 1 to 10 mg/mL, preferably 5 mg/mL.

The second embodiment of the present invention is a vaccine composition that comprises an adjuvant composition comprising citrullines and an antigen.

An antigen may be any that is usually contained in a vaccine including, for instance, carbohydrates, glycolipids, glycoproteins, lipids, lipoproteins, phospholipids, peptides, polypeptides, proteins, polynucleotides, oligonucleotides, and derivatives thereof. As used herein, "peptides" refers to those consisting of 2 to several tens amino acids whereas "polypeptides" refers to those consisting of several tens or more amino acids. Among the antigens listed above, proteins, polypeptides and peptides are preferable. Peptides may preferably be used as an antigen since an adjuvant composition comprising citrullines of the present invention may exert an antibody-producing effect especially when peptides are used as an antigen.

An antigen may be obtained by either genetic recombination, chemical synthesis, or from naturally occurring substance.

An antigen may be pathogens (viruses, bacteria, fungi, parasitic microorganisms), virus-like particles, virosomes, cancer cells, allergens, or an antigen derived from self-molecules.

An antigen derived from pathogens may be a subunit antigen, a peptide antigen, an inactivated pathogen, an attenuated pathogen or a recombinant antigen.

Virus includes, for instance, hepatitis virus, RS virus, adenovirus, avulavirus, isavirus, canine distemper virus, influenza virus A-C, equine arteritis virus, Ebola virus, enterovirus, calicivirus, coronavirus, monkey immunodeficiency virus, thogotovirus, Deng virus, toga virus, avian infectious synovial bursa disease virus, avian pneumovirus (formerly turkey rhinotracheitis virus), nipah virus, Newcastle disease virus, pneumovirus, feline infectious peritonitis virus, feline leukemia virus, Norwalk virus, papilloma virus, papovavirus, parainfluenza virus types 1-3, parvovirus, picornavirus, human cytomegalovirus, human immunodeficiency virus, porcine respiratory and reproduction syndrome virus, flavivirus, henipavirus, hepadnavirus, herpes virus, Hendra virus, poliovirus, Marek's disease virus, metapneumovirus, morbillivirus, rhinovirus, rubulavirus, respirovirus, retrovirus, rotavirus, vaccinia virus, yellow fever virus, infectious rhinotracheitis virus, rinderpest virus, rabies virus, varicellovirus, encephalitis virus, rubella virus, measles virus and mumps virus, preferably influenza virus.

Influenza virus is RNA envelop virus with a size of the viral particle of about 100 nm belonging to the family Orthomyxoviridae family and is classified into type A, B or C depending on antigenicity of the internal protein, among which type A may cause infection both in human and animals and show high diversity. Type A has two kinds of envelop glycoproteins, hemagglutinin (HA) and neuraminidase (NA). There are 16 subtypes for HA and 9 subtypes for NA due to distinction of antigenicity. A combination of these subtypes results in many serotypes of type A influenza virus. When influenza virus in combination of subtypes not occurred in the past appears, influenza may become extremely widespread due to lack of immunity thereto, so-called a pandemic of influenza.

Influenza virus as used herein as an antigen may be of any type, subtype or strain. An antigen derived from influenza virus includes HA, NA, M1, M2 and NP, most preferably HA and M2. The reason is that a vaccine comprising HA as an antigen would have versatility since HA is used as an antigen in the conventional influenza vaccine compositions. Besides, as disclosed in WO 2011024748 (Patent reference 4), M2 protein with less mutation in its amino acid sequence among influenza viruses may be useful from the viewpoint that it may endow immunity against a wide range of influenza viruses. M2 protein may be a peptide which corresponds to a region consisting of 23 amino acid residues generated after removal of a hydrophobic transmembrane domain from M2 (M2e; SEQ ID NO: 1; N-terminus SLLTEVETPIRNEWGCRCNDSSD C-terminus), or M2e peptide with addition or insertion of 1 or several cysteine residues, or M2e peptide with addition of a cysteine-containing peptide for the purpose of enhancement of antigenicity of M2e peptide. The M2e peptide modified with cysteine as above includes those peptides disclosed in WO 2011024748 (Patent reference 4), specifically, synthetic peptide M2eC212223 (SEQ ID NO: 2; N-terminus SLLTEVETPIRNEWGCRCNCDCSCSD C-terminus) in which cysteine residue is inserted between No. 20 and No. 21, between No. 21 and No. 22, and between No. 22 and No. 23, respectively, counted from the N-terminus of M2e.

For preparing an antigen from influenza virus, any known method may be used without particular limitation. For instance, a virus strain isolated from animals infected with influenza virus or patients suffering from influenza may be infected to chicken eggs or cells for culture in a conventional manner and an antigen may be prepared from a purified viral stock solution. Alternatively, an antigen may also be prepared from a genetically recombined virus or a specific antigen produced or expressed in various cells.

A self-molecule for use as an antigen includes amyloid β peptide or a peptide consisting of a portion of the amino acid sequence of amyloid β peptide. Amyloid β peptide or a peptide consisting of a portion of the amino acid sequence of amyloid β peptide may be those peptides with addition or insertion of 1 or several cysteine residues or with addition of a cysteine-containing peptide. These peptides include those disclosed in WO 2008133208 (Patent reference 5). Specifically, amyloid β peptide may be amyloid β peptide consisting of 42 amino acid residues (SEQ ID NO: 3; N-terminus DAEFRHDSGYEVHHQKLVFFAEDVGSNKGAI-IGLMVGGVVIA C-terminus). A peptide consisting of a portion of the amino acid sequence of amyloid β peptide may be a peptide consisting of 28 amino acid residues counted from the N-terminus (SEQ ID NO: 4; N-terminus DAEFRHDS-GYEVHHQKLVFFAEDVGSNK C-terminus). A peptide with addition of 1 or several cysteine residues may be 28AACys peptide (SEQ ID NO: 5; N-terminus DAEFRHDS-GYEVHHQKLVFFAEDVGSNKC C-terminus) in which one cysteine residue is added to the C-terminus of a peptide consisting of 28 amino acid residues counted from the N-terminus.

Bacteria include, for instance, *Actinobacillus pleuropneumoniae*, *Alloiococcus otitis*, Influenza bacteria (including both those type-classifiable and those non-type-classifiable), *Yersinia* bacteria, *Chlamydia psittaci*, *Campylobacter*, *Chlamydia pneumonia* pathogen, *Clostridia species*, *Vibrio cholerae*, *Salmonella choleraesuis*, *Giardia*, diphtheria bacteria, *Pseudomonas* species, *Streptococcus gordonii*, *Streptococcus thermophilus*, *Streptococcus bovis*, *Streptococcus agalactiae*, *Chlamydia trachomatis*, *Mycobacterium avium* group, *Salmonella typhimurium*, *Pasteurella haemolytica*, *Pasteurella multocida*, *Mycobacterium tuberculosis*, *Streptococcus suis*, *Proteus vulgaris*, *Proteus mirabilis*, *Haemophilus somnus*, *Helicobacter pylori*, *Borrelia burgdorferi*, *Mycoplasma gallisepticum*, *Moraxella catarrhalis*, *Leptospira interrogans*, *Staphylococcus aureus*, *Streptococcus pyogenes*, *Neisseria meningitidis*, *Shigella*, *Streptococcus equi*, *Escherichia coli*, anthrax, typhoid bacteria, *Clostridium tetani*, *Streptococcus pneumoniae*, *Bordetella pertussis*, *Staphylococcus epidermidis*, *Streptococcus faecalis*, *Streptococcus viridans*, and *Neisseria gonorrhoeae*.

Parasites include, for instance, *Entamoeba histolytica*, *Plasmodium*, *Leishmania major*, *Ascaris*, *Trichuris*, *Giardia*, *Schistosoma*, *Cryptosporidium*, *Trichomonas*, *Toxoplasma*, and *Pneumocystis carinii*.

A concentration of an antigen contained in a vaccine composition of the present invention may suitably vary depending upon the kind of an antigen, a way of administration of a vaccine composition, a dosage form, and the like.

A weight ratio of an antigen and citrullines contained in a vaccine composition of the present invention may be 1:N wherein N is preferably 100 or more, 200 or more, 300 or more, 333 or more, 400 or more, 800 or more, 3000 or more, 3333 or more, 6000 or more, 6666 or more, 10000 or more, 13000 or more, 13333 or more, 160000 or more, or 16666 or more. A weight ratio of an antigen and citrullines may also be 1:A to 1:B wherein A and B are different numeric selected from the group consisting of 100, 200, 300, 333, 400, 800, 3000, 3333, 6000, 6666, 10000, 13000, 13333, 16000 and 16666 and wherein A is smaller than B.

In case that an antigen is an HA protein, a weight ratio of an antigen and citrullines contained in a vaccine composition of the present invention may be 1:N wherein N is preferably 300 or more, 333 or more, 3000 or more, 3333 or more, 6000 or more, 6666 or more, 10000 or more, 13000 or more, 13333 or more, 160000 or more, or 16666 or more. A weight ratio of an antigen and citrullines may also be 1:A to 1:B wherein A and B are different numeric selected from the group consisting of 300, 333, 3000, 3333, 6000, 6666, 10000, 13000, 13333, 16000 and 16666 and wherein A is smaller than B.

In case that an antigen is a peptide, a weight ratio of an antigen and citrullines contained in a vaccine composition of the present invention may be 1:N wherein N is preferably 100 or more, 200 or more, 400 or more, or 800 or more. A weight ratio of an antigen and citrullines may also be 1:A to 1:B wherein A and B are different numeric selected from the group consisting of 100, 200, 400 and 800 and 16666 and wherein A is smaller than B.

In case that an antigen is an M2e peptide, a weight ratio of an antigen and citrullines contained in a vaccine composition of the present invention may be 1:N wherein N is preferably 200 or more.

In case that an antigen is an amyloid β peptide, a weight ratio of an antigen and citrullines contained in a vaccine composition of the present invention may be 1:N wherein N is preferably 100 or more, 200 or more, 400 or more, or 800 or more. A weight ratio of an antigen and citrullines may also be 1:A to 1:B wherein A and B are different numeric selected from the group consisting of 100, 200, 400 and 800 and 16666 and wherein A is smaller than B.

A dose of an antigen of a vaccine composition of the present invention may suitably vary depending upon the kind of an antigen, a way of administration of a vaccine composition, a dosage form, and the like.

A vaccine composition of the present invention may comprise a single antigen or a combination of plural antigens. In case that a vaccine composition of the present invention comprises a combination of plural antigens, it may comprise plural antigens of different types from the same viral or bacterial origin or plural antigens from different viral or bacterial origins. In case of a vaccine composition of influenza virus, it may preferably comprise different types of antigens from type A and type B influenza virus.

A dosage form of a vaccine composition may be such that citrullines and an antigen are formulated in a single container or an adjuvant composition comprising citrullines and an immunogenic composition comprising an antigen are formulated in separate containers. A dosage form after formulation may be, for instance, liquid, powder (lyophilized powder, dried powder), capsule, tablet, lyophilized form, and the like.

A dosage form of an adjuvant composition and a vaccine composition may be, for instance, liquid, powder (lyophilized powder, dried powder), capsule, tablet, lyophilized form, and the like.

An adjuvant composition and a vaccine composition may comprise a pharmaceutically acceptable carrier in addition to citrullines and an antigen. A pharmaceutically acceptable carrier may be any carrier that is usually used for production of a vaccine. Specifically, the carrier includes saline, buffered saline, dextrose, water, glycerol, isotonic aqueous buffer, and a combination thereof. An adjuvant composition and a vaccine composition may further comprise an emulsifier, a preservative (e.g. thimerosal), an isotonicity agent, a pH regulator and an inactivating agent (e.g. formalin) as appropriate.

An object to which an adjuvant composition and a vaccine composition are to be administered may be any organism that may be immunized including human and other mammals (e.g. domestic animals, pets, and wild animals).

A route of administration of an adjuvant composition and a vaccine composition includes, for instance, percutaneous, sublingual, eye drop, intracutaneous, intramuscular, oral, enteral, nasal, intravenous, subcutaneous, intraperitoneal, inhalation from mouth to the lung, and the like.

An adjuvant composition and a vaccine composition may be administered with e.g. stent, catheter, transdermal patch, microneedle, transplantable sustained release device, syringe, syringe with microneedle, no needle device, or spray. In case that an antigen and an adjuvant composition are formulated in separate containers, the antigen and the adjuvant composition may be administered simultaneously or one of them may be administered followed by the other in a defined interval.

The present invention is explained in more detail by means of the following Examples but is not limited thereto.

Example 1

A citrulline solution for use as an adjuvant was prepared as described below. L-Citrulline (Sigma, C7629-1G) was dissolved in distilled solution for injection (manufactured by Otsuka Pharmaceutical Co., Ltd.) at a final concentration of 80 mg/mL. The solution was aseptically filtered with 0.22 μm and stored at −20° C. by lyophilization until use.

(1) Preparation of Composition Comprising Citrullines

For an antigen, an HA antigen of influenza virus (strain: A/Solomon; component: 1200 μg/mL HA) was prepared. The HA antigen was mixed with various concentrations of citrulline to prepare Compositions 1 to 4 as shown in Table 1 (Composition 1 not containing citrulline). As a control, a mixture of the HA antigen and Alum adjuvant (IMJECT ALUM/mixture of aluminum hydroxide and magnesium hydroxide (PIERCE) or ALHYDROGEL/aluminium hydroxide wet gel suspension (BRENNTAG)) was prepared (Control in Table 1).

TABLE 1

| Immunization groups | Components (Weight ratio to antigen) | Dose | O.D. Mean | Standard error |
|---|---|---|---|---|
| Composition 1 | 3 μg/mL HA | 0.3 μg/body HA | 1.541 | 0.132 |
| Composition 2 | 0.1 mg/mL Citrulline 3 μg/mL HA (1:33) | 10 μg/body Citrulline 0.3 μg/body HA | 1.509 | 0.300 |
| Composition 3 | 1 mg/mL Citrulline 3 μg/mL HA (1:333) | 100 μg/body Citrulline 0.3 μg/body HA | 2.057 | 0.174 |
| Composition 4 | 10 mg/mL Citrulline 3 μg/mL HA (1:3333) | 1000 μg/body Citrulline 0.3 μg/body HA | 2.861 | 0.038 |
| Control | 1 mg/mL Alum 3 μg/mL HA (1:333) | 100 μg/body Alum 0.3 μg/body HA | 2.938 | 0.050 |

(2) Immunization of Mice and Recovery of Serum

Compositions 1 to 4 or Control were administered to mice at 100 μL per mouse as described below (a dose per mouse is described in Table 1). Female BALB/c mice of 6 weeks old were weighed and uniformly divided into 4 groups with each group consisting of three mice. Each individual mouse was identified with an animal marker. At the day of administration of test samples, blood was taken from the orbital sinus of mice using a capillary under inhalation anesthesia with isoflurane. After centrifugation, aliquot of sera were taken in tubes. Each 0.1 mL of the test samples were taken in disposable 1 mL syringes (Terumo) and administered subcutaneously at the back of neck of mice. On Day 14 after administration of the test samples, mice were subject to laparotomy under inhalation anesthesia with isoflurane and whole blood was taken from the caudal vena cava in the peritoneal. The blood was left to stand at room temperature for more than 30 minutes and after centrifugation (3000 rpm, 10 minutes) sera were isolated. An antibody to HA antigen in the thus obtained sera was measured by ELISA as described below.

(3) Measurement of Anti-HA Antibody Titer by ELISA

The same antigen as used for immunization at 1 μg/mL was put to ELISA plate at 50 μL/well and left to stand at 4° C. overnight for immobilization by natural adsorption. The plate was washed with PBS (prepared on the day) three times and thereto was added BLOCKER™ Casein in PBS/blocking buffer (Thermo)", which in more detail is 1% (w/v) casein (Hammarsten grade) in 100 mM sodium phosphate, 150 mM NaCl, pH 7.4 containing KATHON® Anti-microbial Agent at 200 μL/well for reaction at room temperature for 1 hour. After washing the plate with PBS three times, antisera (Day 0, 14) diluted 200-fold with BLOCKER™ Casein in PBS/blocking buffer (Thermo)", which in more detail is 1% (w/v) casein (Hammarsten grade) in 100 mM sodium phosphate, 150 mM NaCl, pH 7.4 containing KATHON® Anti-microbial Agent were added to the plate at 50 μL/well for reaction at room temperature for 2 hour. Anti-mouse IgG-POD-labeled antibody (Thermo) diluted 2000-fold with BLOCKER™ Casein in PBS/blocking buffer (Thermo)", which in more detail is 1% (w/v) casein (Hammarsten grade) in 100 mM sodium phosphate, 150 mM NaCl, pH 7.4 containing KATHON® Anti-microbial Agent was added at 50 μL/well for reaction at room temperature for 1 hour. After washing four times with PBS, substrate TMB (BIOFX (SurModics)) was added at 50 μL/well for reaction at room temperature for 15 minutes. Then, 1N $H_2SO_4$ was added at 50 μL/well to stop the reaction. Absorbance at 450 nm was measured.

(4) Results

The results of ELISA are shown in Table 1. In the groups of immunization with both citrulline and an antigen, particularly in the groups with administration of citrulline at 100 μg/body or 1000 μg/body, an adjuvant effect was apparently observed as compared to the group with administration of an antigen alone. Specifically, an antibody-producing effect was about 1.3-fold higher for the group with administration of 100 μg/body citrulline and about 1.9-fold higher for the group with administration of 1000 μg/body citrulline as compared to the group with administration of an antigen alone. In particular, an adjuvant effect was observed for the group with administration of 1000 μg/body citrulline at the same extent as that of Alum adjuvant. It was also observed that the antibody production increased as the dose of citrulline increased.

Example 2

As an adjuvant effect could be seen for citrulline as shown in the results of Example 1, its optimum amount was investigated. In Example 1, the dose of 1000 μg/body citrulline was found to exhibit the highest adjuvant effect when varying doses from 10 to 1000 μg/body were examined. Thus, an effect with a higher dose of citrulline was investigated.

(1) Preparation of Composition Comprising Citrullines

With the procedures as described in Example 1, Compositions 5 to 10 with varying concentrations of citrulline were prepared (Table 2; Composition 5 not containing citrulline).

TABLE 2

| Immunization groups | Components (Weight ratio to antigen) | Dose |
|---|---|---|
| Composition 5 | 3 μg/mL HA | 0.3 μg/body HA |
| Composition 6 | 10 mg/mL Citrulline 3 μg/mL HA (1:3333) | 1 mg/body Citrulline 0.3 μg/body HA |
| Composition 7 | 20 mg/mL Citrulline 3 μg/mL HA (1:6666) | 2 mg/body Citrulline 0.3 μg/body HA |
| Composition 8 | 30 mg/mL Citrulline 3 μg/mL HA (1:10000) | 3 mg/body Citrulline 0.3 μg/body HA |
| Composition 9 | 40 mg/mL Citrulline 3 μg/mL HA (1:13333) | 4 mg/body Citrulline 0.3 μg/body HA |
| Composition 10 | 50 mg/mL Citrulline 3 μg/mL HA (1:16666) | 5 mg/body Citrulline 0.3 μg/body HA |

(2) Immunization of Mice and Recovery of Serum

With the procedures as described in Example 1, Compositions 5 to 10 were administered to mice at 100 μL per mouse and sera were recovered (a dose per mouse is described in Table 2).

(3) Measurement of Anti-HA Antibody Titer by ELISA

With the procedures of ELISA as described in Example 1, an antibody titer was measured.

(4) Results

Figure 1:
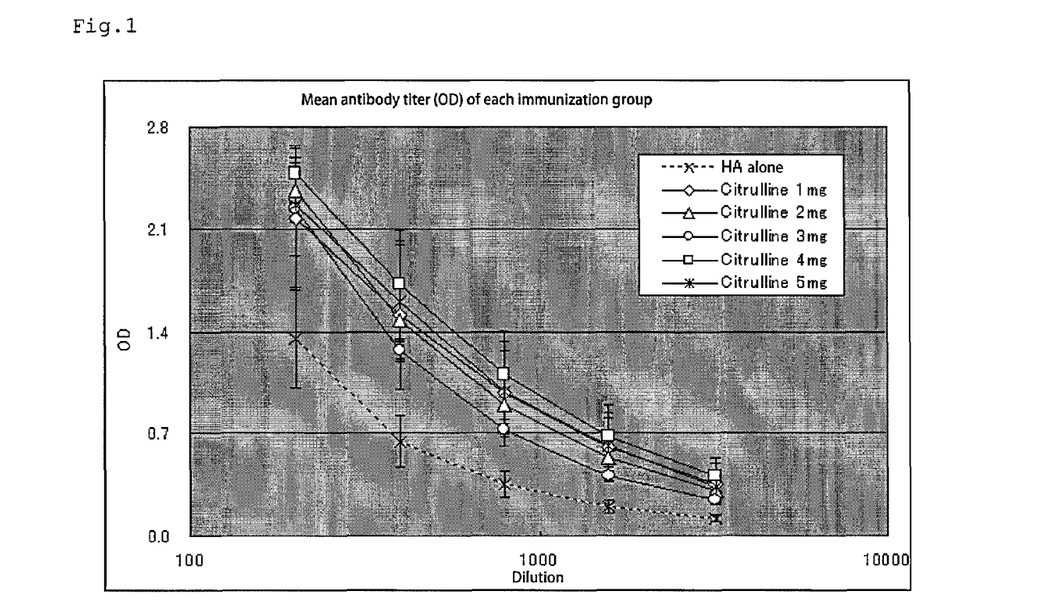
FIG. 1 shows results of measurement of antibody titer against HA antigen when citrulline is administered to mice at 1 to 5 mg/body.

The results of ELISA are shown in FIG. 1. In all groups with administration of citrulline, an adjuvant effect was observed. In this range, dose dependency could be seen to some extent.

Example 3

(1) Preparation of Composition Comprising Citrullines

For an antigen, synthetic peptide M2eC212223 (SEQ ID NO: 2; N-terminus SLLTEVETPIRNEWGCRCNCDC-SCSD C-terminus) was used in which cysteine residue was inserted between No. 20 and No. 21, between No. 21 and No. 22, and between No. 22 and No. 23, respectively, counted from the N-terminus of a region consisting of 23 amino acid residues from M2 protein of type A influenza virus which region is presented on the viral surface (M2e; SEQ ID NO: 1; N-terminus SLLTEVETPIRNEWGCRCNDSSD C-terminus).

As described in WO 2011024748 (Patent reference 4), M2eC212223 peptide was synthesized. The synthesized peptides were prepared at 5 mg/mL with nitrogen gas-substituted distilled water for injection containing 1 mM EDTA and stored as a stock solution at less than −80° C. until use. Composition 11 which does not contain citrulline as a test substance and Composition 12 which is mixed with the citrulline solution as prepared in Example 1 were prepared (Table 3).

TABLE 3

| Immunization groups | Components (Weight ratio to antigen) | Dose |
|---|---|---|
| Composition 11 | 200 µg/mL M2eC212223 | 20 µg/mL M2eC212223 |
| Composition 12 | 40 mg/mL Citrulline 200 µg/mL M2eC212223 (1:200) | 4 mg/mL Citrulline 20 µg/mL M2eC212223 |

(2) Immunization of Mice and Recovery of Serum

Immunization of mice was performed as described below. Female BALB/c mice of 7 weeks old were divided into two groups with each group consisting of five mice. Each individual mouse was identified with an animal marker. The test samples were taken in disposable 1 mL syringes (Terumo) and administered subcutaneously at the back of neck of mice at 0.1 mL per mouse (a dose per mouse is described in Table 3). The test samples were administered twice at a 2-week interval. A week after the second administration, mice were subject to laparotomy under anesthesia with SOMNOPEN-TYL/pentobarbital sodium (Kyoritsu Seiyaku Corporation) and whole blood was taken from the caudal vena cava in the peritoneal. Isolation of sera was performed as described in Example 1.

(3) Measurement of Anti-M2e Antibody Titer by ELISA

With the procedures as described in WO 2011024748 (Patent reference 4), an antibody titer to M2e in sera was measured. Specifically, M2e was diluted with 0.1 M Carbonate buffer, pH9.6 at 2 µg/mL, added to 96-well plate (Nunc, IMMOBILIZER™ Amino) at 100 µL/well and left to stand at 4° C. overnight for immobilization. Next day, each well was washed three times with 300 µL of phosphate buffer containing 0.05% Tween 20 (PBST). Each 300 µL/well of monoethanolamine (Wako Pure Chemical Industries, Ltd.) diluted with 0.1 M Carbonate buffer, pH9.6 at 10 mM was added and the plate was left to stand at room temperature for 1 hour. Thereafter, 10 mM monoethanolamine was sufficiently removed and the samples diluted with PBST were added at 100 µL/well (each sample in duplicate). After reaction at room temperature for 1 hour, the added diluted sera were discarded and the plate was washed three times with PBST at 300 µL/well. After washing, the washing solution within each well was sufficiently removed and HRP-labeled anti-mouse IgG goat antibody (American Qualex, A131PS) diluted 2000-fold with PBST was added at 100 µL/well for reaction at room temperature for 1 hour. After reaction, the dilution solution of the labeled antibody was discarded and the plate was washed twice with PBST at 300 µL/well and twice with the same amount of distilled water. A solution of chromogenic substrate TMB+ (Dako) was added at 100 µL/well for reaction at room temperature for 30 minutes under light shielding. Thereafter, 1N sulfuric acid was added at 100 µL/well to stop the development. Absorbance at 450 nm (OD450) was measured.

(4) Results

Figure 2:
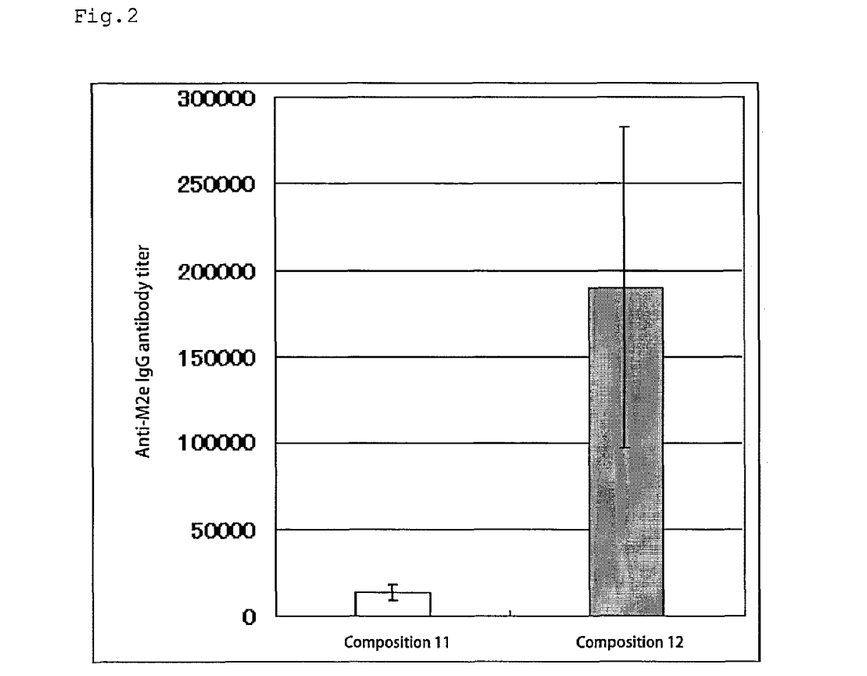
FIG. 2 shows results of measurement of antibody titer against M2e when citrulline is administered to mice at 4 mg/body.

The results of ELISA are shown in FIG. 2. An antibody-producing effect with the use of citrulline as an adjuvant was about 14-fold higher than that with no use of citrulline. This proves that citrulline may exhibit an adjuvant effect not only to HA antigen of influenza virus but also to the synthetic peptide M2eC212223.

Example 4

(1) Preparation of Composition Comprising Citrullines

For an antigen was used a synthetic peptide 28AACys (SEQ ID NO: 5; N-terminus DAEFRHDSGYEVH-HQKLVFFAEDVGSNKC C-terminus) in which one cysteine residue was added to the C-terminus of a peptide consisting of 28 amino acid residues counted from the N-terminus (SEQ ID NO: 4; N-terminus DAEFRHDS-GYEVHHQKLVFFAEDVGSNK C-terminus) which was a portion of amyloid β peptide consisting of 42 amino acid residues (SEQ ID NO: 3; N-terminus DAEFRHDSGYEVH-HQKLVFFAEDVGSNKGAIIGLMVGGVVIA C-terminus).

The synthetic peptide was synthesized as described in WO 2008133208 (Patent reference 5) (Hokkaido System Science Co., Ltd.) and prepared at 5 mg/mL with saline as a stock solution and stored at less than −80° C. until use. For application, the solution was prepared at 10 µg/body.

A citrulline solution for use as an adjuvant was prepared as described below. L-Citrulline (Sigma, C7629-1G) was dissolved in saline (Otsuka Pharmaceutical Co., Ltd.) at a final concentration of 50 mg/mL. The solution was stored at −30° C. by lyophilization until use. Likewise, L-ascorbic acid (Wako Pure Chemical Industries, Ltd.) was dissolved in saline (Otsuka Pharmaceutical Co., Ltd.) at a final concentration of 50 mg/mL and the solution was stored at 4° C. under refrigeration until use. For control, Alum (ALHYDROGEL/ aluminium hydroxide wet gel suspension) was used. The citrulline solution, 28AACys and the ascorbic acid solution were mixed together to prepare Controls 1 and 2 and Compositions 13 to 18 as shown in Table 4.

TABLE 4

| Immunization groups | Components (Weight ratio to antigen) | Dose (200 µL) | Mean | Standard error |
|---|---|---|---|---|
| Control 1 | 50 µg/mL 28AACys | 10 µg/body 28AACys | 425 | 596 |
| Control 2 | 5 mg/mL Alum 50 µg/mL 28AACys (1:100) | 1 mg/body Alum 10 µg/body 28AACys | 506 | 533 |

TABLE 4-continued

| Immunization groups | Components (Weight ratio to antigen) | Dose (200 µL) | Mean | Standard error |
|---|---|---|---|---|
| Composition 13 | 5 mg/mL Citrulline<br>50 µg/mL 28AACys<br>(1:100) | 1 mg/body Citrulline<br>10 µg/body 28AACys | 4935 | 3976 |
| Composition 14 | 10 mg/mL Citrulline<br>50 µg/mL 28AACys<br>(1:200) | 2 mg/body Citrulline<br>10 µg/body 28AACys | 17954 | 1838 |
| Composition 15 | 20 mg/mL Citrulline<br>50 µg/mL 28AACys<br>(1:400) | 4 mg/body Citrulline<br>10 µg/body 28AACys | 53450 | 49062 |
| Composition 16 | 40 mg/mL Citrulline<br>50 µg/mL 28AACys<br>(1:800) | 8 mg/body Citrulline<br>10 µg/body 28AACys | 60217 | 39928 |
| Composition 17 | 5 mg/mL L-Ascorbic acid<br>50 µg/mL 28AACys<br>(1:100) | 1 mg/body L-Ascorbic acid<br>10 µg/body 28AACys | 1639 | 3013 |
| Composition 18 | 5 mg/mL Citrulline<br>5 mg/mL L-Ascorbic acid<br>50 µg/mL 28AACys<br>(1:100:100) | 1 mg/body Citrulline<br>1 mg/body L-Ascorbic acid<br>10 µg/body 28AACys | 19941 | 18839 |

Immunization of mice was performed as described below. Male C57BL/6 mice of 7 weeks old were divided into eight groups with each group consisting of four mice. Each individual mouse was identified with an animal marker. The compositions were administered subcutaneously to the abdomen of mice using 1 mL syringes for tuberculin (Terumo; SS-01T2613S) at 200 µL per mouse (a dose per mouse is described in Table 4). Mice were immunized twice at a 2-week interval. On 14 Day after the second immunization, blood was taken from the caudal vena cava in the peritoneal under anesthesia with pentobarbital sodium (Kyoritsu Seiyaku Corporation; SOMNOPENTYL) and the mice were sacrificed. The blood taken was transferred to MICROTINA/ blood collection tube (BECTON DICKINSON) and coagulated sufficiently at room temperature and then centrifuged (5000 rpm, 10 minutes). The isolated sera were dispensed into two 0.5 mL tubes and stored at −80° C. until measurement. Antibodies to Aβ peptide in sera were measured by ELISA as described below.

(3) Measurement of Anti-Aβ IgG Antibody Titer by ELISA

Aβ peptide (1-40 amino acid sequence: N-terminus DAE-FRHDSGYEVHHQKLVFFAEDVGSNKGAI-IGLMVGGVV (SEQ ID NO: 6), synthesized by Hokkaido System Science Co., Ltd.) was diluted with 0.1 M Carbonate buffer, pH9.6 at 10 µg/mL, added to 8 well strips (Nalgen-Nunc, IMMOBILIZER™ Amino) at 100 µL/well and left to stand at 4° C. overnight for immobilization. Next day, each well was washed three times with 300 µL of PBS containing 0.05% Tween 20 (PBST). Each 300 µL/well of 10 mM ethanolamine was added and the plate was left to stand at room temperature for 1 hour. Thereafter, 10 mM ethanolamine was sufficiently removed and the samples diluted with PBST by 50-fold to 10000-fold were added at 100 µL/well (each sample in duplicate). After reaction at room temperature for 1 hour, the added diluted sera were discarded and the plate was washed three times with PBST at 300 µL/well. After washing, the washing solution within each well was sufficiently removed and HRP-labeled anti-mouse IgG goat antibody (American Qualax, A131PS) diluted 2000-fold with the dilution solution for sample was added at 100 µL/well for reaction at room temperature for 1 hour. After reaction, the dilution solution of the labeled antibody was discarded and the plate was washed twice with PBST at 300 µL/well and twice with the same amount of distilled water. A solution of chromogenic substrate TMB+ (Dako) was added at 100 µL/well for reaction at room temperature for 30 minutes under light shielding. Thereafter, 1N sulfuric acid was added at 100 µL/well to stop the development. Absorbance at 450 nm (OD450) was measured.

Commercially available anti-Aβ monoclonal antibody (CHEMICON; MAB1560) was used as standard serum. Standard serum was diluted with PBST to 0.156, 0.3125, 0.625, 1.25, 2.5, 5 and 10 ng/mL to prepare standards for measuring antibody titer. Each of the diluted samples in duplicate were measured for OD450 concurrently with measurement of anti-Aβ IgG antibody in each of the sample mouse sera. Anti-Aβ IgG antibody titer in each of the sample mouse sera was calculated from the obtained standard units and the standard line of OD450.

(4) Results

The calculated anti-Aβ antibody titers in mouse sera in the respective immunization groups are shown in Table 4. The groups with administration of citrulline (Compositions 13-16 and 18) showed an enhanced antibody-producing effect as compared to the group with no administration of the adjuvant (Control 1). Specifically, an extremely enhanced antibody-producing effect was observed about 11.6-fold higher for the group with administration of 1 mg/body (Composition 13), about 42.2-fold higher for the group with administration of 2 mg/body (Composition 14), about 125.8-fold higher for the group with administration of 4 mg/body (Composition 15), and about 141.7-fold higher for the group with administration of 8 mg/body (Composition 16) as compared to the group with no administration of the adjuvant.

The group with administration of L-ascorbic acid alone exhibited almost no antibody-producing effect (from comparison of Control 1 and Composition 17). However, the group with administration of both L-ascorbic acid and citrulline exhibited an enhanced antibody-producing effect about 4.0-fold higher as compared to the group with administration of citrulline alone (from comparison of Compositions 13 and 18), about 12.1-fold higher as compared to the group with administration of L-ascorbic acid alone (from comparison of Compositions 17 and 18), about 39.4-fold higher as compared to the group with administration of Alum (from comparison of Control 2 and Composition 18), and about 46.9-fold higher as compared to the group with no administration of citrulline (from comparison of Control 1 and Composition 18).

Both the group with administration of citrulline and the group with administration of both citrulline and ascorbic acid showed a higher antibody-producing effect than that of the group with administration of Alum, i.e. about 9.8-fold higher for Composition 13, about 35.5-fold higher for Composition 14, about 105.6-fold higher for Composition 15, about 119-fold higher for Composition 16, and about 39.4-fold higher for Composition 18, thus proving an extremely excellent antibody-producing effect as compared to the conventional Alum adjuvant.

From the results shown in Examples 1, 2, 3 and 4, it was apparently observed that citrulline had an adjuvant effect irrespective of the kind of an antigen. For a specific concentration of citrulline, the effect was equivalent to that of the conventional Alum adjuvant. In particular, in case of a peptide antigen, the effect was higher than that of the conventional Alum adjuvant. Besides, it was found that citrulline exhibited an enhanced adjuvant effect when it was used in combination with ascorbic acid.

In addition, citrulline is highly safe as neither abnormality nor induration that is seen in a topical area where Alum is administered were found in mice administered with citrulline.

INDUSTRIAL APPLICABILITY

The present invention provides an adjuvant composition comprising citrulline and a vaccine composition comprising said adjuvant composition and an antigen. Since citrulline is useful for the living body and is water soluble substance, it becomes possible to provide an adjuvant composition and a vaccine composition that are highly safe and excellent in convenience for compounding as compared to the conventional Alum adjuvant or oily adjuvants.

The invention claimed is:

1. A vaccine composition comprising an adjuvant composition comprising an adjuvant effective amount of citrulline and a hemagglutinin antigen from influenza virus, wherein the adjuvant effective amount of citrulline ranges from 1 mg/mL to 50 mg/mL.

2. The vaccine composition according to claim 1, wherein the citrulline is at least one member selected from the group consisting of L-citrulline, D-citrulline, L-thiocitrulline, L-thiohomocitrulline, S-methyl-L-thio-citrulline and S-ethyl-L-thiocitrulline.

3. The vaccine composition according to claim 2, wherein the citrulline is L-citrulline or D-citrulline.

4. The vaccine composition according to claim 1, comprising 5 mg/mL to 45 mg/mL of the citrulline.

5. The vaccine composition according to claim 1, further comprising an antioxidant.

6. The vaccine composition according to claim 5, wherein the antioxidant is ascorbic acid.

7. The vaccine composition according to claim 5, wherein a weight ratio of the citrulline to the antioxidant is 1:2 to 2:1.

8. The vaccine composition according to claim 5, comprising 1 to 10 mg/mL of the antioxidant.

9. The vaccine composition according to claim 1, wherein a weight ratio of the antigen to the citrulline is 1:N wherein N is 100 or more.

10. The vaccine composition according to claim 9, wherein a weight ratio of the antigen to the citrulline is 1:N wherein N is 300 or more.

11. The vaccine composition according to claim 10, wherein a weight ratio of the antigen to the citrulline is 1:N wherein N is 3000 or more.

12. A process for preparing the vaccine according to claim 1, comprising adding a citrulline to a hemagglutinin antigen from influenza virus, wherein the amount of citrulline in said vaccine ranges from 1 mg/mL to 50 mg/mL.

13. The process according to claim 12, wherein the citrulline is at least one member selected from the group consisting of L-citrulline, D-citrulline, L-thiocitrulline, L-thiohomocitrulline, S-methyl-L-thio-citrulline and S-ethyl-L-thiocitrulline.

14. The process according to claim 13, wherein the citrulline is L-citrulline or D-citrulline.

15. The process according to claim 12, wherein a weight ratio of the antigen to the citrulline is 1:N wherein N is 100 or more.

16. The process according to claim 15, wherein a weight ratio of the antigen to the citrulline is 1:N wherein N is 300 or more.

17. The process according to claim 12, further comprising adding an antioxidant to the vaccine.

18. The process according to claim 17, wherein the antioxidant is ascorbic acid.

19. The process according to claim 17, wherein the citrulline and the antioxidant are in a weight ratio of 1:2 to 2:1, and are added to the hemagglutinin antigen.

20. The process according to claim 17, wherein the antioxidant is added at a concentration of 1 to 10 mg/mL.

* * * * *